(12) United States Patent
Limketkai et al.

(10) Patent No.: US 9,834,803 B2
(45) Date of Patent: Dec. 5, 2017

(54) METHODS TO ISOLATE CYCLODEXTRINS

(71) Applicant: PanaceaNano, Inc., Aliso Viejo, CA (US)

(72) Inventors: Benjie N. Limketkai, Hesperia, CA (US); Youssry Y. Botros, Aliso Viejo, CA (US)

(73) Assignee: PanaceaNano, Inc., Aliso Viejo, CA (US)

( * ) Notice: Subject to any disclaimer, the term of this patent is extended or adjusted under 35 U.S.C. 154(b) by 0 days.

(21) Appl. No.: 15/220,618

(22) Filed: Jul. 27, 2016

(65) Prior Publication Data

US 2017/0058306 A1  Mar. 2, 2017

Related U.S. Application Data

(60) Provisional application No. 62/212,026, filed on Aug. 31, 2015.

(51) Int. Cl.
  *C12P 19/22* (2006.01)
  *C12P 19/04* (2006.01)
  *C08B 37/16* (2006.01)
  *C12P 9/00* (2006.01)

(52) U.S. Cl.
  CPC .......... *C12P 19/04* (2013.01); *C08B 37/0012* (2013.01); *C12P 9/00* (2013.01)

(58) Field of Classification Search
  None
  See application file for complete search history.

(56) References Cited

U.S. PATENT DOCUMENTS

| | | | |
|---|---|---|---|
| 2,886,446 A | 5/1959 | Kramer et al. | |
| 3,258,400 A | 6/1966 | Houlihan | |
| 3,920,849 A | 11/1975 | Marmo et al. | |
| 3,939,099 A | 2/1976 | Tusa et al. | |
| 4,252,986 A | 2/1981 | Klein et al. | |
| 4,303,787 A | 12/1981 | Horikoshi et al. | |
| 4,384,898 A | 5/1983 | Okada et al. | |
| 4,568,560 A | 2/1986 | Schobel | |
| 4,808,232 A | 2/1989 | Beesley | |
| 4,835,105 A | 5/1989 | Seres et al. | |
| 4,849,400 A | 7/1989 | King | |
| 5,051,305 A | 9/1991 | Whitaker, Sr. | |
| 5,238,915 A | 8/1993 | Fuwa et al. | |
| 6,110,449 A | 8/2000 | Bacon et al. | |
| 6,172,037 B1 | 1/2001 | Perring et al. | |
| 6,177,413 B1 | 1/2001 | Blahut | |
| 6,458,754 B1 | 10/2002 | Velazquez et al. | |
| 6,558,706 B2 | 5/2003 | Kantor et al. | |
| 8,709,072 B2 | 4/2014 | Rahi et al. | |
| 8,871,473 B2 * | 10/2014 | Wu | C12P 19/18 127/40 |
| 9,085,460 B2 * | 7/2015 | Stoddart | B01J 20/226 |
| 9,399,803 B2 * | 7/2016 | Stoddart | C22B 11/04 |
| 2003/0092600 A1 | 5/2003 | Shepherd, Jr. | |
| 2005/0255069 A1 | 11/2005 | Muller | |
| 2008/0054089 A1 | 3/2008 | Oldfield et al. | |
| 2008/0206823 A1 | 8/2008 | Jacobson et al. | |
| 2011/0052650 A1 | 3/2011 | Morris et al. | |
| 2012/0070904 A1 | 3/2012 | Stoddart et al. | |
| 2013/0171228 A1 | 7/2013 | Morris | |
| 2013/0313193 A1 | 11/2013 | Nair et al. | |
| 2014/0105842 A1 | 4/2014 | Pan et al. | |
| 2014/0220112 A1 | 8/2014 | Szoka, Jr. et al. | |
| 2014/0311297 A1 | 10/2014 | Stoddart et al. | |
| 2015/0150981 A1 | 6/2015 | Gref et al. | |
| 2015/0322174 A1 | 11/2015 | Stoddart et al. | |
| 2017/0203073 A1 | 7/2017 | Dor-Zidon | |

FOREIGN PATENT DOCUMENTS

| | | |
|---|---|---|
| CN | 104888235 A | 9/2015 |
| JP | H 0576756 A | 3/1993 |
| WO | 2007035596 A2 | 3/2007 |
| WO | 2016010522 A1 | 1/2016 |

OTHER PUBLICATIONS

International Search Report and Written Opinion mailed in corresponding International Patent Application No. PCT/US16/44184 dated Oct. 7, 2016 (11 pages).
Smaldone, R.A., et al., "Metal-Organic Frameworks from Edible Natural Products" *Angew. Chem. Int. Ed.*, 49:8630-8634 (2010).
Gassensmith, J. J., et al., "Strong and Reversible Binding of Carbon Dioxide in a Green Metal-Organic Framework" *Journal of the American Chemical Society* 133:15312-15315 (2011).
Gassensmith, J. J., et al., "A Metal-Organic Framework-Based Material for Electrochemical Sensing of Carbon Dioxide" *J. Am. Chem. Soc.* 136:8277-8282 (2014).
Gassensmith, J. J., et al., "A Metal-Organic Framework-Based Material for Electrochemical Sensing of Carbon Dioxide" *J. Am. Chem. Soc.* pp. S1-S12 (support document).
Forgan, R.S., et al., "Nanoporous Carbohydrate Metal-Organic Frameworks" *J. Am. Chem. Soc.* 134:406-417 (2012).
Wind, R.D., et al., "Engineering of factors determining α-amylase and cyclodextrin glycosyltransferase specificity in the cyclodextrin glycosyltransferase from *Thermoanaerobacterium thermosulfurigenes* EM1" *Eur. J. Biochem.* 253:598-605 (1998).
Liu, Z., et al., "Second-Sphere Coordination Revisited" *Chimia* 68:5 315-320 (2014).
Liu, Z. and Stoddart, J.F., "Extended metal-carbohydrate frameworks*" *Pure Appl. Chem.* 2014, 86, 1323-1334.
McKinlay, et al.; "BioMOFs: Metal-Organic Frameworks for Biological and Medical Applications"; 2010; pp. 6260-6266.

\* cited by examiner

*Primary Examiner* — Hope Robinson

(57) ABSTRACT

This disclosure relates to methods of isolating CDs. The method includes contacting a CD production mixture containing αCD, βCD, γCD, and CD production byproducts with a metal salt; and forming CD-MOF complexes containing at least a metal cation and a plurality of CD components.

34 Claims, 1 Drawing Sheet

METHODS TO ISOLATE CYCLODEXTRINS

CROSS REFERENCE TO RELATED APPLICATION

Pursuant to 35 U.S.C. §119(e), this application claims priority to U.S. Provisional Application Ser. No. 62/212,026, filed Aug. 31, 2015, the contents of which are hereby incorporated by reference.

TECHNICAL FIELD

This disclosure relates to methods to isolate cyclodextrins (CDs), e.g., αCDs, βCDs, and/or γCDs, by forming CD-metal organic framework (CD-MOF) complexes.

BACKGROUND

Cyclodextrins (cyclic dextrins, cyclic oligosaccharides, CDs) are cyclic structures composed of D-glucopyranosyl residues linked in a ring by α-1,4 glycosidic bonds. Glucose molecules, bonded together in the ring, form a hollow, circular, truncated cone with a hydrophobic interior and a hydrophilic exterior. This structure gives CDs the ability to host guest molecules (complexant) within their cavity. Due to this ability to form inclusion compounds (complex) with a wide variety of chemicals, thereby acting as a carrier to encapsulate, stabilize, and/or alter the chemical and physical properties, e.g., volatility and solubility, of the guest molecules, CDs have been widely used in the agricultural, food, pharmaceutical, cosmetic, and chemical industries. The common αCD, βCD, and γCD consist of six, seven, and eight glucopyranose units in their ring, respectively.

SUMMARY

This disclosure is based on the unexpected discovery that CDs can be isolated from a CD production mixture by forming CD-MOF complexes. The present methods can be used to efficiently isolate CDs (such as γCD) with significantly reduced time and cost. Further, the present methods can be used to isolate CDs on a large scale, e.g., commercial production scale. In some embodiments, one advantage of the methods described herein is the use of non-toxic solvents to isolate CDs, e.g., αCD and/or γCD, that can be safely and efficiently used for human consumption, e.g., in pharmaceutical or food applications. For example, ethanol can be used to form and isolate CD-MOF complexes, and any trace amounts of ethanol can be readily removed by evaporation. In addition, the solvent used in the methods described herein can be removed from the CD isolated by such a method relatively easily (e.g., by evaporation). In contrast, conventional methods of producing CDs typically requires insertion of an organic agent into the CD cavity to form a "complex" with the CD. Subsequent removal of this organic agent from within the CD cavity is difficult and time-consuming, often requiring steam distillation or liquid-liquid extraction with a solvent. For production of γCD in particular, large cyclic complexing agents (e.g., cyclododecanone and cyclohexadec-8-en-1-one) are required to fit and complex within the large γCD cavity, and removal of such agents is difficult, and there is no economical solvent recovery process available to recycle the complexing agents for reuse.

In one aspect, this disclosure provides methods that include contacting a CD production mixture with a metal salt; and forming CD-MOF complexes. The CD production mixture contains αCD, βCD, γCD, and CD production byproducts. The CD-MOF complexes include αCD-MOF and γCD-MOF complexes and each CD-MOF complex contains at least a metal cation and a plurality of CD components.

In another aspect, this disclosure features methods that include treating a composition containing a polysaccharide with a cyclodextrin glycosyltransferase (CGTase) to form a CD production mixture; and forming CD-MOF complexes. The forming includes contacting a CD production mixture with a metal salt. The CD production mixture contains αCD, βCD, γCD, and CD production byproducts, and each CD-MOF complex contains at least a metal cation and a plurality of CD components.

In still another aspect, this disclosure provides methods that include contacting a CD production mixture with a square planar metal complex to form an αCD-MOF complex; and separating the αCD-MOF complex from the CD production mixture. The CD production mixture contains αCD, βCD, γCD, and CD production byproducts, and the αCD MOF complex contains at least a metal cation and a plurality of αCD components.

Embodiments can include one or more of the following features.

In some embodiments, the CD production mixture is derived from a polysaccharide. In some embodiments, the polysaccharide is starch, glycogen, cellulose, amylose, or any combination thereof.

In some embodiments, the methods include treating the polysaccharide with a CGTase to form the CD production mixture. For example, the CGTase is an αCGTase or a γCGTase.

In some embodiments, the methods include treating a composition comprising a polysaccharide with an amylase prior to treating the polysaccharide with a CGTase. In some instances, the amylase is an α-amylase, β-amylase, or γ-amylase.

In some embodiments, the metal salt contains a metal cation, e.g., Group IA metal cation, Group IIA metal cation, or transition metal cation. In some embodiments, the metal cation is $K^+$, $Rb^+$, $Na^+$, $Cs^+$, $Li^+$, $Mg^{2+}$, $Cd^{2+}$, $Sn^{2+}$, $Ag^+$, $Yb^+$, $Ba^{2+}$, $Sr^{2+}$, $Ca^{2+}$, $Pb^{2+}$, or $La^{3+}$.

In some embodiments, the metal salt contains an anion such as $OH^-$, $Cl^-$, $Br^-$, $C_7H_5O_2^-$, $CO_3^{2-}$, $F^-$, $S^{2-}$, $CrO_4^{2-}$, and $CN^-$.

In some embodiments, the metal salt is potassium hydroxide, rubidium hydroxide, potassium chloride, potassium benzoate, cesium hydroxide, or sodium carbonate.

In some embodiments, forming CD-MOF complexes includes contacting the CD production mixture with a first solvent containing $C_{1-10}$ alcohol, $C_{1-10}$ alkane, methylene chloride, acetone, acetic acid, acetonitrile, benzene, toluene, dimethylformamide, or a mixture thereof to form the αCD-MOF and γCD-MOF complexes.

In some embodiments, the first solvent is vapor diffused into the CD production mixture.

In some embodiments, the method includes treating the CD production mixture with an amylase prior to or after contacting the CD production mixture with the first solvent. In some embodiments, the amylase is an α-amylase, β-amylase, or γ-amylase.

In some embodiments, the methods include collecting the αCD-MOF and γCD-MOF complexes from the CD production mixture by filtration and/or centrifugation.

In some embodiments, the methods include selectively dissolving the αCD-MOF complex in a second solvent with heating.

In some embodiments, the second solvent contains $C_{1-10}$ alcohol, $C_{1-10}$ alkane, methylene chloride, acetone, acetic acid, acetonitrile, benzene, toluene, dimethylformamide, or a mixture thereof.

In some embodiments, the methods include dissolving the γCD-MOF complex in water to produce a γCD aqueous solution.

In some embodiments, the methods include passing the γCD aqueous solution through an ion exchange resin to isolate γCD.

In some embodiments, the methods include crystallizing βCD from the CD production mixture prior to contacting the CD production mixture with the metal salt. In some embodiments, the methods include collecting βCD crystals from the CD production mixture by filtration and/or centrifugation.

In some embodiments, the square planar metal complex contains a noble metal. For example, the noble metal can be gold, platinum, or palladium. In some embodiments, the square planar metal complex is potassium tetrabromoaurate or potassium tetrachloroaurate.

In some embodiments, the methods include treating a composition containing a polysaccharide with a CGTase to form the CD production mixture.

In some embodiments, the methods include treating the composition with an amylase prior to or after contacting the CD production mixture with the square planar metal complex. For example, the amylase can be an α-amylase, β-amylase, or γ-amylase.

In some embodiments, separating the αCD-MOF complex from the CD production mixture includes filtration and/or centrifugation.

In some embodiments, the methods include dissolving the αCD-MOF complex in water with heating to produce an αCD aqueous solution.

In some embodiments, the methods include passing the αCD aqueous solution through an ion exchange resin to isolate αCD.

In some embodiments, the methods include contacting the CD production mixture with a metal salt after separating the αCD-MOF complex from the CD production mixture.

In some embodiments, the methods include contacting the CD production mixture and the metal salt with a solvent containing $C_{1-10}$ alcohol, $C_{1-10}$ alkane, methylene chloride, acetone, acetic acid, acetonitrile, benzene, toluene, dimethylformamide, or a mixture thereof to form a γCD-MOF complex.

As used herein, the term "polysaccharide" refers to a saccharide polymer containing two or more simple sugar units bound together by glycosidic linkages and upon hydrolysis, gives the constituent monosaccharides. The polysaccharide can be an oligosaccharide or a disaccharide. Examples of polysaccharides include starch, glycogen, cellulose, amylose, and any combination thereof.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features, objects, and advantages of the invention will be apparent from the description, drawings, and claims.

DETAILED DESCRIPTION

Figure 3:
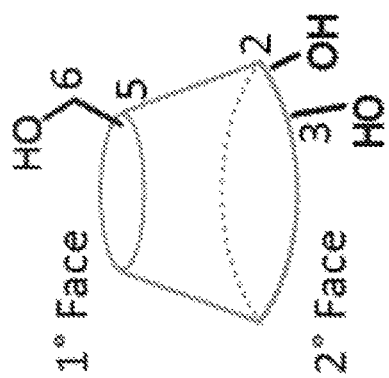
FIG. 3 illustrates the eight monosaccharide residues in γCD form a truncated cone with the C6 hydroxy (OH) groups constituting the primary (1°) face and the C2 and C3 OH groups constituting the secondary (2°) face.

This disclosure relates generally to methods to isolate CDs, e.g., αCDs, βCDs, and/or γCDs, by forming CD-MOF complexes. In general, the CD isolation methods include contacting a CD production mixture with a metal salt and forming CD-MOF complexes.

Isolation of CDs can start by producing a CD production mixture from at least one polysaccharide, e.g., starch, glycogen, cellulose, amylose, or any combination thereof. The polysaccharide can be obtained from a natural source, e.g., potato, rice, wheat, and maize. Alternatively or in addition, the polysaccharide can be chemically synthesized. Regardless of the source, the polysaccharide can be provided in a composition (e.g., an aqueous solution) at a concentration ranging from at least about 10% by weight (e.g., at least about 15%, at least about 20% by weight, at least about 25% by weight, or at least about 30% by weight) to at most about 50% by weight (e.g., at most about 40% by weight, at most about 35% by weight, at most about 30% by weight, or at most about 25% by weight). For example, the composition can include from at least about 10% by weight to at most about 30% by weight of the polysaccharide. The polysaccharide can be disposed in a solvent, e.g., water, at a suitable temperature (e.g., from at least about 20° C. to at most about 90° C.) to produce a composition (e.g., a solution, suspension, or dispersion).

To produce a CD production mixture containing αCD, βCD, and γCD, a composition containing a polysaccharide can be treated with at least one CD glycosyltransferase (CGTase). CGTase (EC 2.4.1.19) is a bacterial enzyme capable of catalyzing the synthesis of CDs by cyclizing part of a (1→4)-alpha-D-glucan chain by formation of a (1→4)-alpha-D-glucosidic bond. CGTase is an enzyme common in many bacterial species, in particular the *Bacillus* genus (e.g., *B. macerans, B. coagulans, B. alkalophilic, B. circulans, B. macerans*, and *B. stearothermophilus*), as well as in some archaea. CGTase can be isolated from bacterial fermentation cultures of *Bacillus*. See, e.g., Jozsef Szejtli, Cyclodextrin Technology, Springer, 1988; Karl-Heinz Fromming and Jozsef Szejtli, Cyclodextrin in Pharmacy, Kluwer Academic Publishers, 1994; James N. BeMiller and Roy L. Whistler, Starch: Chemistry and Technology, Academic Press, 2009; and Zheng-Yu Jin, Cyclodextrin Chemistry: Preparation and Application, World Scientific Publishing, 2013, the contents of which are hereby incorporated by reference in their entirety. Alternatively, CGTase can be purchased from commercial sources, e.g., SBH Sciences, Natick, Mass. The CGTase can be an αCGTase, a βCGTase, or a γCGTase, which preferentially form αCD, βCD, and γCD, respectively upon contacting a polysaccharide. In some embodiments, the composition containing the polysaccharide can be treated with a mixture of CGTases to form a CD production mixture.

In some embodiments, a CGTase is added to the composition containing a polysaccharide (e.g., a polysaccharide aqueous solution) to produce a CD production mixture. The CD production mixture can include different CDs, e.g., αCDs, βCDs, and γCDs, and CD production byproducts. The CD production byproducts can include, e.g., unconverted polysaccharides, oligosaccharides, disaccharides (e.g., maltose), monosaccharides (e.g., glucose). The relative ratios and yields of the different CDs will depend on the starting polysaccharide substrate and reaction conditions, such as the selected CGTase enzyme, polysaccharide concentration, reaction time, temperature, pH, additives, and precipitants. To improve yield and reduce purification cost, production ratios can be biased to a particular type of CD by using selective α, β, and γCGTase enzymes that predominantly produce α, β, and γCDs, respectively, depending on the CD of interest.

In some embodiments, the CD isolation methods described herein can optionally include a step of treating the composition containing a polysaccharide with an amylase prior to contacting the composition with a CGTase. The amylase can be an α-amylase, β-amylase, and/or γ-amylase. The α-amylases (EC 3.2.1.1) break down long-chain polysaccharides. For example, α-amylase can digest amylose to yield maltotriose and maltose. Because α-amylase can act anywhere on the polysaccharide substrate, α-amylase tends to be faster-acting than β-amylase. In animals, α-amylase is a major digestive enzyme, and its optimum pH is 6.7-7.0. β-amylase (EC 3.2.1.2) works from the non-reducing end of the polysaccharide substrate and catalyzes the hydrolysis of the second α-1,4 glycosidic bond, cleaving off two glucose units (maltose) at a time. The optimum pH for β-amylase is 4.0-5.0. In contrast, γ-amylase (EC 3.2.1.3) can cleave α(1-6) glycosidic linkages, as well as the last α(1-4)glycosidic linkages at the nonreducing end of polysaccharide substrates, to yield glucose. The γ-amylase has optimal activity at around pH 3.0. These three amylases can be readily obtained from commercial sources, e.g., Sigma-Aldrich Co. As known in the art, amylase activity can be stopped by acidification to a pH lower than optimal activity for the amylase, e.g., about pH 1.0 to pH 2.0 and/or by raising the temperature to at least about 55° C. (e.g., at least about 60° C., at least about 70° C., at least about 80° C., or at least about 90° C.) and/or at most about 100° C. (e.g., at most about 60° C., at most about 70° C., at most about 80° C., or at most about 90° C.) to denature the amylase. Optimal digestion of the polysaccharide can be readily determined by a skilled practitioner. In some embodiments, the composition containing a polysaccharide can be treated with a mixture of amylases prior to contacting the composition with a CGTase. Without wishing to be bound by theory, it is believed that an advantage of this additional amylase-treating step is that the amylase can break down the polysaccharide to make it easier for the CGTase to convert the polysaccharide to form CDs, thereby increasing the yield of the CDs.

In an exemplary method, after contacting the composition containing a polysaccharide with a CGTase, a CD production mixture containing αCD, βCD, γCD, and CD production byproducts thus formed can be contacted with a metal salt in order to form CD-MOF complexes. For example, the metal salt can have a Group IA metal cation, Group IIA metal cation, or transition metal cation. In some instances, the metal cation is $K^+$, $Rb^+$, $Na^+$, $Cs^+$, $Li^+$, $Mg^{2+}$, $Cd^{2+}$, $Sn^{2+}$, $Yb^+$, $Ba^{2+}$, $Sr^{2+}$, $Ca^{2+}$, $Pb^{2+}$, or $La^{3+}$. In some embodiments, the metal salt has an $OH^-$, $Cl^-$, $Br^-$, $C_7H_5O_2^-$, $CO_3^{2-}$, $F^-$, $S^{2-}$, $CrO_4^{2-}$, or $CN^-$ anion. As an example, the metal salt can be potassium hydroxide, rubidium hydroxide, potassium chloride, potassium benzoate, cesium hydroxide, or sodium carbonate.

In some embodiments, CD-MOF complexes can be formed by the following method. At ambient temperatures and pressures, the CD production mixture containing a metal salt obtained above can be contacted with a first solvent. The first solvent can contain $C_{1-10}$ alcohol (e.g., ethanol), $C_{1-10}$ alkane, methylene chloride, acetone, acetic acid, acetonitrile, benzene, toluene, dimethylformamide, or a mixture thereof. In the some embodiments, the first solvent can include a mixture of water and at least one of the solvents described above. In some embodiments, the first solvent can be vapor diffused into the CD production mixture to form CD-MOF complexes (e.g., αCD-MOF and γCD-MOF complexes) in crystalline form with a relative large crystal size.

Other methods of forming CD-MOF complexes include those described in U.S. Pat. No. 9,085,460, WO 2014/172667, and Liu et al. (*Pure Appl Chem* 86:1323-1334, 2014), the contents of which are hereby incorporated by reference in their entireties.

The CD-MOF complexes generally include at least one metal cation (e.g., a plurality of metal cations) and a plurality of CD components (such as those of Formula (I) below). The at least one metal cation is generally coordinated with the plurality of CD molecules or CD derivatives. In general, the CD-MOF complexes are porous.

Figure 2:
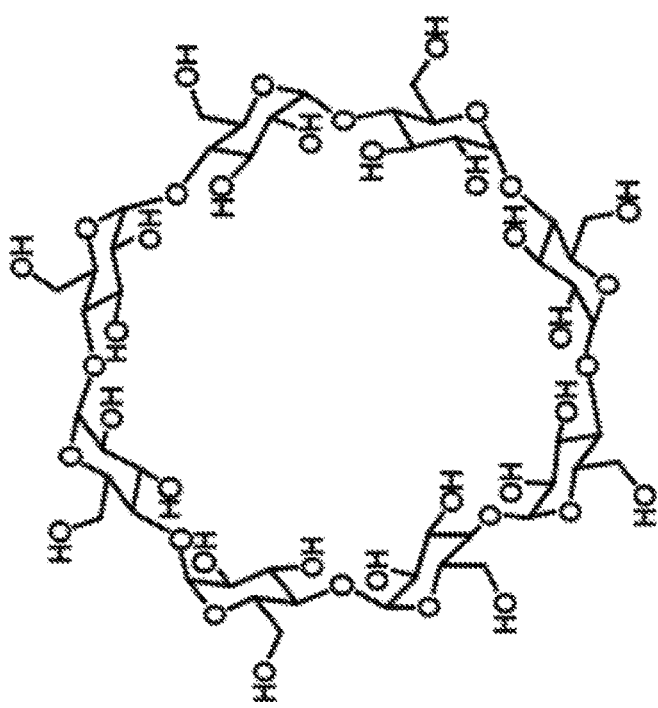
FIG. 2 illustrates the structure of a γCD ring.
Figure 1:
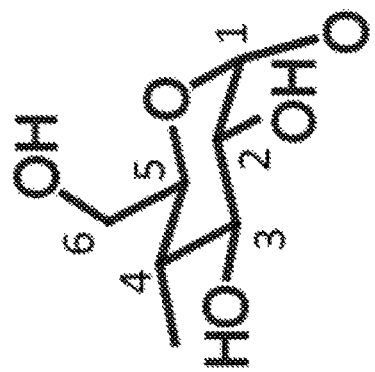
FIG. 1 illustrates the structure of α-1,4-linked D-glucopyranosyl residue.

In general, the main building block for CD-MOF complexes is CD, a cyclic oligosaccharide that includes monosaccharide residues linked in a circular ring. Suitable CDs that can be used in the CD-MOF complexes include, for example, α, β, and γCDs. FIG. 1 illustrates the structure of α-1,4-linked D-glucopyranosyl residue. FIG. 2 illustrates the structure of a γCD ring. FIG. 3 illustrates the eight monosaccharide residues in γCD form a truncated cone with the C6 hydroxy (OH) groups constituting the primary (1°) face and the C2 and C3 OH groups constituting the secondary (2°) face. CDs can be mass-produced through enzymatic degradation of a renewable source (e.g., starch). In some embodiments, a CD-MOF complex can be made from one or more CD derivatives (such as those shown in Formula (I) below). Without wishing to be bound by theory, it is believed that the CD rings in a γCD-MOF complex adopt the faces of a cube, with their primary (1°) faces pointing towards the interior of the cube and their secondary (2°) faces pointing outward. Further, without wishing to be bound by theory, it is believed that the CD rings in a γCD-MOF complex are linked together by coordination of the metal cations to the primary C6 OH groups and the glycosidic ring oxygen atoms. The individual cubes pack to form the body-centered cubic crystal through coordination of more alkali metal cations to the C2 and C3 OH groups of the secondary faces of the CD rings.

In some embodiments, the CD-MOF complexes described herein include a CD component and a metal-containing component. The metal-containing component can have the formula MN. M can be a Group IA metal cation, Group IIA metal cation, or a transition metal cation, and N can be an organic or inorganic, monovalent or multivalent anion. Suitable inorganic anions include, for example, hydroxide, chloride, bromide, sulfinate, carbonate, fluoride, sulfide, chromate, and cyanide. Suitable organic anions include, for example, benzoate, azobenzene-4,4'-dicarboxylate, acetate, and oxalate. The CD component of the CD-MOF complexes can be a compound of the Formula (I):

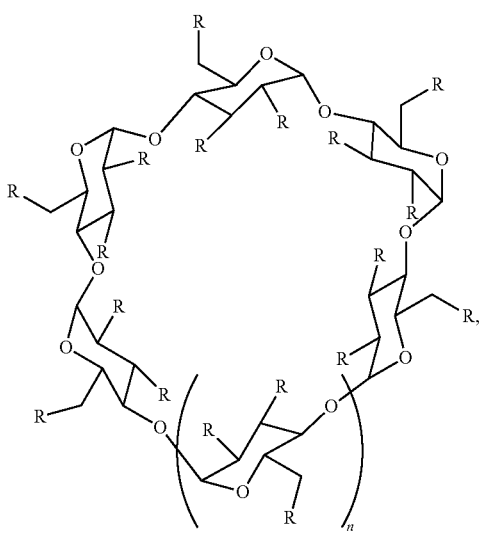

(I)

in which n=0-10; R is selected from the group consisting of —OH; —NR'R''; $C_1$-$C_{18}$ alkyl optionally substituted with one, two, three, four or five $R_1$ groups; $C_2$-$C_{18}$ alkenyl optionally substituted with one, two, three, four or five $R_1$ groups; $C_2$-$C_{18}$ alkynyl optionally substituted with one, two, three, four or five $R_1$ groups; $C_1$-$C_{18}$ alkoxy optionally substituted with one, two, three, four or five $R_1$ groups; —S(=O)$_2$R'; —S(=O)OR'; —S(=O)R'; —C(=O)OR'; —CN; —C(=O)R'; —SR', —N=N$^+$=N$^-$; —NO$_2$, —OSO$_2$R'; —C(=O)OR'; —O(=S)SR'; —P(=O)(OR')$_2$; —OP(=O)(OR')$_2$; —P(=O)(OR')R''; —N=R'R''; —NR'P(OR'')(OR'''); —OC(=O)NR'R''; aryl optionally substituted with one, two, three, four or five $R_2$ groups; heteroaryl optionally substituted with one, two, three, four or five groups independently selected from $R_2$ groups; and cycloalkyl optionally substituted with one, two, three, four or five groups independently selected from $R_2$ groups; each $R_1$ group is independently selected from the group consisting of hydroxyl, halo, $C_1$-$C_6$ alkoxy, —NR'R''; —S(=O)$_2$R'; —S(=O)OR'; —S(=O)R'; —C(=O)OR'; —CN; —C(=O)R'; —SR', —N=N$^+$=N$^-$; —NO$_2$, —OSO$_2$R'; —C(=O)OR'; —O(=S)SR'; —P(=O)(OR')$_2$; —OP(=O)(OR')$_2$; —P(=O)(OR')R''; —N=R'R''; —NR'P(OR'')(OR'''); —OC(=O)NR'R''; aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; each $R_2$ group is independently selected from the group consisting of $C_1$-$C_6$ alkyl, $C_2$-$C_6$ alkenyl, $C_2$-$C_6$ alkynyl, hydroxyl, halo, $C_1$-$C_6$ alkoxy, —NR'R''; —S(=O)$_2$R'; —S(=O)OR'; —S(=O)R'; —C(=O)OR'; —CN; —C(=O)R'; —SR', —N=N$^+$=N$^-$; —NO$_2$, —OSO$_2$R'; —C(=O)OR'; —O(=S)SR'; —P(=O)(OR')$_2$; —OP(=O)(OR')$_2$; —P(=O)(OR')R''; —N=R'R''; —NR'P(OR'')(OR'''); —OC(=O)NR'R''; aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; and wherein each R', R'', and R''' are independently selected from the group consisting of H, $C_1$-$C_6$ alkyl, and aryl. Examples of compounds of Formula (I) include α, β, and γCDs.

As used herein, the term "alkyl" refers to a straight or branched chain alkyl radical. Examples include, but are not limited, to methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Each alkyl group may be optionally substituted with one, two, or three substituents such as a halo, cycloalkyl, aryl, alkenyl, or alkoxy group.

As used herein, the term "lower alkenyl" refers to a straight or branched hydrocarbon radical having one or two double bonds and includes, for example, ethenyl, propenyl, 1-but-3-enyl, 1-pent-3-enyl, and 1-hex-5-enyl. The alkenyl group can also be optionally mono-, di-, or trisubstituted with, for example, halo, aryl, cycloalkyl, or alkoxy.

As used herein, the term "alkynyl" refers to a straight or branched hydrocarbon radical having one or two triple bonds and includes, for example, propynyl and 1-but-3-ynyl. The alkynyl group can also be optionally mono-, di-, or trisubstituted with, for example, halo, aryl, cycloalkyl, or alkoxy.

As used herein, the term "alkoxy" refers to an —O-alkyl group in which the alkyl is as defined above.

As used herein, the term "halo" or "halogen" refers to a halogen radical of fluorine, chlorine, bromine, or iodine.

As used herein, the term "aryl" refers to an aromatic carbocyclic radical having a single ring (e.g., phenyl), multiple rings (e.g., biphenyl), or multiple fused rings in which at least one is aromatic (e.g., 1,2,3,4-tetrahydronaphthyl).

As used herein, the term "heteroaryl" refers to one aromatic ring or multiple fused aromatic ring systems of 5-, 6-, or 7-membered rings containing at least one and up to four heteroatoms (e.g., nitrogen, oxygen, or sulfur). Examples include, but are not limited to, furanyl, thienyl, pyridinyl, pyrimidinyl, benzimidazolyl, and benzoxazolyl.

As used herein, the term "cycloalkyl" refers to a carbocylic radical having a single ring (e.g., cyclohexyl), multiple rings (e.g., bicyclohexyl) or multiple fused rings (e.g., decahydronaphthalenyl). In addition, the cycloalkyl group may have one or more double bonds.

In some embodiments, the CD isolation methods described herein can optionally include a step of treating the CD production mixture with an amylase (1) after the CD production mixture is formed but prior to contacting the CD production mixture and the metal salt with a first solvent or (2) after contacting the CD production mixture and the metal salt with a first solvent. Without wishing to be bound by theory, it is believed that this amylase-treating step can break down unconverted polysaccharides (e.g., unconverted oligosaccharides or disaccharides) in the CD production mixture to form CD production byproducts that have a higher solubility in the CD production mixture, thereby allowing the CD-MOF complexes to be separated from the CD production mixture more easily.

In some embodiments, after contacting the CD production mixture with the first solvent, a mixture of solid CD-MOF complexes (which can include predominantly αCD-MOF and γCD-MOF complexes) can be collected from the CD production mixture by filtration and/or centrifugation. The CD-MOF complexes thus formed can be nano-crystalline or crystalline. The collected αCD-MOF complex can then be separated from the mixture by selective dissolution in a second solvent to produce an αCD solution. Examples of suitable second solvents include $C_{1-10}$ alcohol (e.g., ethanol), $C_{1-10}$ alkane, methylene chloride, acetone, acetic acid, acetonitrile, benzene, toluene, dimethylformamide, and a mixture thereof. In some embodiments, the second solvent can include a mixture of water and one or more of the solvents described above to produce an αCD aqueous solution. In some embodiments, the dissolution of the αCD-MOF complex can be performed at an elevated temperature. For example, the αCD-MOF complex can be selectively dissolved in the second solvent at a temperature from at least about 25° C. (e.g., at least about 30° C., at least about 50° C., at least about 60° C., at least about 80° C., at least about 90° C., at least about 100° C., at least about 130° C., at least about 150° C., or at least about 180° C.) to at most about 200° C. (e.g., at most about 180° C., at most about 150° C., at most about 130° C., at most about 100° C., at most about 90° C., at most about 80° C., at most about 60° C., at most about 50° C., or at most about 30° C.). In some embodiments, the αCD solution thus formed can be separated from the solid γCD-MOF complex by filtration and/or centrifugation. In some embodiments, αCD can be isolated from the αCD solution by passing the αCD solution through an ion exchange resin. αCD can also be separated from the metal salt by crystallization since αCD is typically not as soluble as the metal salt. Alternatively, αCD can be separated from the metal salt through use of molecular sieves since αCD is generally much larger than the metal salt. The solid γCD-MOF complex can be dissolved in a suitable solvent (e.g., water) to produce a γCD solution (e.g., a γCD aqueous solution). The γCD can then be isolated from the γCD solution by passing the γCD solution through an ion exchange resin. In some embodiments, γCD can also be separated from the metal salt by crystallization since γCD typically is not as soluble as the metal salt. Alternatively, γCD can be separated from the metal salt through use of molecular sieves since γCD is generally much larger than the metal salt.

In some embodiments, prior to contacting the CD production mixture with the first solvent to form CD-MOF complexes, insoluble impurities in the mixture (if present) can be removed from the CD production mixture by filtration and/or centrifugation to improve the purity of the CD-MOF complexes thus formed.

In some embodiments, βCD can be removed from the CD production mixture before contacting the CD production mixture with the first solvent to form solid αCD-MOF and γCD-MOF complexes. In such embodiments, to remove βCD, the CD production mixture can be concentrated by vacuum distillation and/or can have its temperature lowered to a suitable temperature (e.g., from about 25° C. to about 4° C.) to crystallize βCD. Crystalline βCDs can then be separated from the CD production mixture by filtration and/or centrifugation, and washed and recrystallized in appropriate solvents for higher purity, as described in Jozsef Szejtli, Cyclodextrin Technology, Springer, 1988; Karl-Heinz Fromming and Jozsef Szejtli, Cyclodextrin in Pharmacy, Kluwer Academic Publishers, 1994; James N. BeMiller and Roy L. Whistler, Starch: Chemistry and Technology, Academic Press, 2009; and Zheng-Yu Jin, Cyclodextrin Chemistry: Preparation and Application, World Scientific Publishing, 2013, the contents of which are hereby incorporated by reference in their entirety. In some embodiments, βCD can be removed from the CD production mixture (e.g., by crystallization) after αCD-MOF and γCD-MOF complexes are formed and removed from the CD production mixture.

Alternatively, in some embodiments of the CD isolation methods described herein, rather than using a metal salt to form a mixture of CD-MOF complexes (which can include both αCD-MOF and γCD-MOF complexes) from the CD production mixture, the αCD-MOF complex can be selectively formed from the CD production mixture using a square planar metal complex without substantially forming a γCD-MOF complex. For example, a composition containing a polysaccharide (e.g., a polysaccharide aqueous solution) can first be treated with a CGTase to form a CD production mixture, as described above. The CD production mixture can be contacted with a square planar metal complex to selectively form an αCD-MOF complex that has at least a metal cation and a plurality of αCD components without substantially forming a γCD-MOF complex. The αCD-MOF complex can then be separated from the CD production mixture.

In some embodiments, upon contacting the CD production mixture with a square planar metal complex, an αCD-MOF complex forms and quickly precipitates out of the CD production mixture. As a non-limiting example, the metal in the square planar metal complex is a noble metal, e.g., gold, platinum, or palladium. For example, the square planar metal complex can be potassium tetrabromoaurate or potassium tetrachloroaurate.

Once the αCD-MOF complex is formed, it can be separated from the CD production mixture by filtration and/or centrifugation. αCD can then be isolated from the αCD-MOF complex thus formed by using the same methods described above (e.g., dissolving the αCD-MOF complex in a suitable solvent to form an αCD solution and then passing the αCD solution through an ion exchange resin to isolate αCD, crystallization, or use of a molecular sieve). The square planar metal complex can be recovered from the ion exchange resin and recycled.

After separating the αCD-MOF complex from the CD production mixture, γCD can be isolated from the CD production mixture by using the same method described above. For example, the CD production mixture can be treated with a metal salt (such as those described herein) and a suitable solvent (such as those described herein) to form a γCD-MOF complex. The metal salt and the solvent can be added simultaneously or sequentially. The γCD-MOF complex thus formed can then be separated from the CD production mixture (e.g., by filtration or centrifugation). The isolated γCD-MOF complex can subsequently be dissolved in a suitable solvent (e.g., water) to form a γCD solution (e.g., a γCD aqueous solution). The γCD solution can then be passed through an ion exchange resin to separate the γCD from the metal salt. Alternatively, as described herein, γCD can be separated from the metal salt by crystallization or use of molecular sieves.

In embodiments where a square planar metal complex is used to isolate αCD, the CD isolation methods described herein can optionally include (1) a step of treating a composition containing a polysaccharide with amylase prior to contacting the composition with a CGTase, (2) a step of treating the CD production mixture with an amylase after the CD production mixture is formed but prior to contacting the CD production mixture and the square planar metal complex with a solvent to form a αCD-MOF complex, (3) a step of treating the CD production mixture with an amylase after the αCD-MOF complex is formed but before the formation of a γCD-MOF complex, or (4) a step of treating the CD production mixture with an amylase after the γCD-MOF complex is formed.

In embodiments where a square planar metal complex is used to isolate αCD, the CD isolation methods described herein can optionally remove βCD from the CD production mixture (1) before forming an αCD-MOF complex, (2) after forming an αCD-MOF complex, but before forming a γCD-MOF complex, or (3) after forming a γCD-MOF complex. For example, to remove βCD before forming an αCD-MOF complex, the CD production mixture can be concentrated by vacuum distillation and/or can have its temperature lowered to a suitable temperature (e.g., from about 25° C. to about 4° C.) to crystallize the βCD. Crystalline βCD can then be separated from the CD production solution by filtration and/or centrifugation. Optionally, the βCD can be washed and recrystallized in suitable solvents for higher purity.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for isolating cyclodextrins, comprising:
    forming an aqueous solution of a cyclodextrin (CD) production mixture with αCD, βCD, and γCD therein;
    adding a square planar metal complex to the aqueous solution of the CD production mixture to selectively form an αCD-metal organic framework (MOF) complex and precipitate the αCD-MOF complex out of the solution as a solid αCD-MOF complex with the βCD, and γCD remaining in the aqueous solution;
    separating the solid αCD-MOF complex from the aqueous solution with the βCD, and the γCD remaining in the aqueous solution;
    adding a solvent and a metal salt to the aqueous solution with the βCD, and γCD remaining therein to selectively form a γCD-MOF complex and precipitate the γCD-MOF complex out of a mixture of the aqueous solution and solvent as a solid γCD-MOF complex with the βCD remaining in the aqueous solution, wherein: the solvent is a $C_{1-10}$ alcohol, $C_{1-10}$ alkane, methylene chloride, acetone, acetic acid, acetonitrile, benzene, toluene, dimethylformamide, or a mixture thereof;
    separating the solid γCD-MOF complex from the mixture of the aqueous solution and solvent with the βCD remaining therein; and
    concentrating or lowering the temperature of the mixture of the aqueous solution and solvent with the βCD remaining therein to precipitate the βCD out of the aqueous solution as solid βCD.

2. The method of claim 1, wherein, forming the aqueous solution of the CD production mixture further comprises:
    treating an aqueous solution of a polysaccharide with a CD glycosyltransferase (CGTase); and then treating the aqueous solution of the polysaccharide with an amylase.

3. The method of claim 1, wherein the metal salt has a metal cation selected from the group consisting of Group IA metal cations, Group IIA metal cations, and transition metal cations.

4. The method of claim 3, wherein the metal cation is $K^+$, $Rb^+$, $Na^+$, $Cs^+$, $Li^+$, $Mg^{2+}$, $Cd^{2+}$, $Sn^{2+}$, $Ag^+$, $Yb^+$, $Ba^{2+}$, $Sr^{2+}$, $Ca^{2+}$, $Pb^{2+}$, or $La^{3+}$.

5. The method of claim 1, wherein the metal salt has an anion selected from the group consisting of $Cl^-$, $Br^-$, $C_7H_5O_2^-$, $F^-$, $S^{2-}$, $CrO_4^{2-}$, and $CN^-$.

6. The method of claim 1, wherein the metal salt is potassium chloride or potassium benzoate.

7. The method of claim 1, wherein the solvent is a $C_{1-10}$ alkane, methylene chloride, acetic acid, benzene, toluene, or a mixture thereof.

8. The method of claim 7, wherein the solvent is vapor diffused into the aqueous solution with the βCD, and the γCD remaining therein.

9. The method of claim 1, wherein, forming the aqueous solution of the CD production mixture further comprises:
    treating an aqueous solution of a polysaccharide with an amylase; and then
    treating the aqueous solution of the polysaccharide with a CD glycosyltransferase (CGTase).

10. The method of claim 9, wherein the amylase is an α-amylase, β-amylase, or γ-amylase.

11. The method of claim 1, further comprising dissolving the solid αCD-MOF complex in a second solvent with heating to form an αCD solution and the passing the αCD solution through an ion exchange resin to isolate the αCD from the αCD solution.

12. The method of claim 11, wherein the second solvent comprises $C_{1-10}$ alcohol, $C_{1-10}$ alkane, methylene chloride, acetone, acetic acid, acetonitrile, benzene, toluene, dimethylformamide, or a mixture thereof.

13. The method of claim 1, further comprising dissolving the solid γCD-MOF complex in water to produce a γCD aqueous solution.

14. The method of claim 13, further comprising passing the γCD aqueous solution through an ion exchange resin to isolate the γCD from the γCD aqueous solution.

15. The method of claim 1, further comprising isolating the solid βCD from the aqueous solution by filtration or centrifugation.

16. A method for isolating cyclodextrins, comprising:
    treating a polysaccharide composition with a cyclodextrin glycosyltransferase (CGTase) to form a cyclodextrin (CD) production mixture; and
    treating the polysaccharide composition with an amylase prior to treating the polysaccharide composition with the CGTase or treating the CD production mixture with an amylase after treating the polysaccharide composition with the CGTase,
    forming CD-metal organic framework (MOF) complexes, the forming comprising contacting a CD production mixture with a metal compound,
    wherein the CD production mixture comprises αCD, βCD, γCD, and CD production byproducts, and each CD-MOF complex comprises at least a metal cation and a plurality of CD components.

17. The method of claim 16, comprising treating the polysaccharide composition with the amylase prior to treating the polysaccharide composition with the CGTase.

18. The method of claim 17, wherein the amylase is an α-amylase, β-amylase, or γ-amylase.

19. The method of claim 16, comprising treating the CD production mixture with the amylase after treating the polysaccharide composition with the CGTase.

20. The method of claim 19, wherein the amylase is an α-amylase, β-amylase, or γ-amylase.

21. A method for isolating cyclodextrins, comprising:
    forming an aqueous solution of a cyclodextrin (CD) production mixture with αCD, βCD, and γCD therein;
    concentrating or lowering the temperature of the CD production mixture to precipitate the βCD out of the aqueous solution as a solid βCD with the αCD, and γCD remaining in the aqueous solution;
    separating the solid βCD from the aqueous solution with the αCD, and γCD remaining therein;

adding a square planar metal complex to the aqueous solution with the αCD, and γCD remaining therein to selectively form an αCD-metal organic framework (MOF) complex and precipitate the αCD-MOF complex out of the aqueous solution as a solid αCD-MOF complex with the γCD remaining in the aqueous solution;

separating the solid αCD-MOF complex from the aqueous solution with the γCD remaining therein;

adding a solvent and a metal salt to the aqueous solution with the γCD remaining therein to form a γCD-MOF complex and precipitate the γCD-MOF complex out of the solution as a solid γCD-MOF complex, wherein the solvent is a $C_{1-10}$ alcohol, $C_{1-10}$ alkane, methylene chloride, acetone, acetic acid, acetonitrile, benzene, toluene, dimethylformamide, or a mixture thereof, and, the metal salt includes a metal cation consisting of Group IA metal cations; and separating the solid γCD-MOF complex from the aqueous solution.

22. The method of claim 21, wherein the square planar metal complex comprises a noble metal.

23. The method of claim 22, wherein the noble metal is gold, platinum, or palladium.

24. The method of claim 21, wherein the square planar metal complex is potassium tetrabromoaurate or potassium tetrachloroaurate.

25. The method of claim 21, wherein, forming the aqueous solution of the CD production mixture further comprises:

treating an aqueous solution of a polysaccharide composition with an amylase; and then treating the polysaccharide composition with a CD glycosyltransferase (CGTase).

26. The method of claim 21, wherein, forming the aqueous solution of the CD production mixture further comprises:

treating the polysaccharide composition with a CD glycosyltransferase (CGTase); and then treating an aqueous solution of a polysaccharide composition with an amylase.

27. The method of claim 26, wherein the amylase is an α-amylase, β-amylase, or γamylase.

28. The method of claim 21, wherein separating the solid αCD-MOF complex from the aqueous solution with the γCD remaining therein comprises filtration or centrifugation.

29. The method of claim 21, further comprising dissolving the solid αCD-MOF complex in water with heating to produce an αCD aqueous solution.

30. The method of claim 29, further comprising passing the αCD aqueous solution through an ion exchange resin to isolate the αCD.

31. The method of claim 21, wherein the solvent is a $C_{1-10}$ alkane, methylene chloride, acetic acid, benzene, toluene, or a mixture thereof.

32. The method of claim 21, further comprising dissolving the solid γCD-MOF complex in water to produce a γCD aqueous solution.

33. The method of claim 32, further comprising passing the γCD aqueous solution through an ion exchange resin to isolate the γCD.

34. The method of claim 21, wherein separating the solid βCD from the aqueous solution further comprises collecting βCD crystals from the aqueous solution with the αCD, and γCD remaining therein by filtration or centrifugation.

* * * * *